United States Patent [19]

Panzeri et al.

[11] Patent Number: 5,212,166
[45] Date of Patent: May 18, 1993

[54] UNSATURATED 17β-SUBSITUTED 3-CARBOXY STEROIDS

[75] Inventors: Achille Panzeri, Merate; Marcella Nesi; Enrico Di Salle, both of Milan, all of Italy

[73] Assignee: Farmitalia Carlo Erba S.r.l., Milan, Italy

[21] Appl. No.: 886,574

[22] Filed: May 21, 1992

[30] Foreign Application Priority Data

May 24, 1991 [IT] Italy .................. MI91A001432

[51] Int. Cl.$^5$ .................. C07J 43/00; C07J 3/00; A61K 31/58
[52] U.S. Cl. .................. 514/176; 540/108; 540/110; 540/113; 552/610
[58] Field of Search ............. 552/610; 540/108, 110, 540/113; 514/176

[56] References Cited

U.S. PATENT DOCUMENTS 5,032,586  7/1991  Metcalf et al. ............ 552/610

FOREIGN PATENT DOCUMENTS 0289327 11/1988 European Pat. Off. .
0414529  2/1991 European Pat. Off. .
0427434  5/1991 European Pat. Off. .
 465141  1/1992 European Pat. Off. ............ 552/610

Primary Examiner—Marianne M. Cintins
Assistant Examiner—Kimberly J. Kestler
Attorney, Agent, or Firm—Nikaido Marmelstein Murray & Oram

[57] ABSTRACT

The present invention concerns steroidic 5α-reductase inhibitors having the following formula (I)

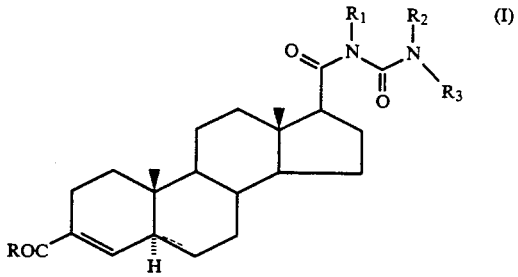

wherein
Y is oxygen or sulphur;
R is a group;
 a) —OR$_4$, wherein R$_4$ is hydrogen or a C$_1$–C$_6$ alkyl group;
 b)

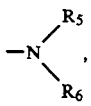

wherein each of R$_5$ and R$_6$, independently, is hydrogen or a C$_1$–C$_6$ alkyl group;
 c)

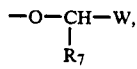

wherein R$_7$ is hydrogen or a C$_1$–C$_6$ alkyl group and W is a group:
 (i)

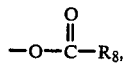

wherein R$_8$ is a C$_1$–C$_6$ alkyl group, a C$_5$–C$_6$ cycloalky group, a C$_6$–C$_6$ cycloalkylalkyl group, a phenyl group or a benzyl group; or
 (ii)

(Abstract continued on next page.)

ABSTRACT

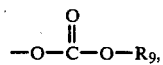

wherein $R_9$ is a $C_1$-$C_6$ alkyl group or a $C_5$-$C_6$ cycloalkyl group; or (iii)

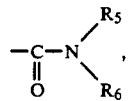

wherein $R_5$ and $R_6$ are as defined above;

d)

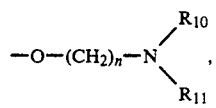

wherein each of $R_{10}$ and $R_{11}$ is, independently, hydrogen or a $C_1$-$C_6$ alkyl group or taken together with the nitrogen atom to which they are linked form a pentatomic or hexatomic saturated heteromonocyclic ring, optionally containing at least one additional heteroatom selected from oxygen and nitrogen, and n is an integer of 2 to 4;

$R_1$ is hydrogen, a $C_1$-$C_6$ alkyl group, a $C_5$-$C_6$ cycloalkyl group, a $C_6$-$C_9$ cycloalkyalkyl group or an aryl group;

each of $R_2$ and $R_3$ is, independently, selected from the group consisting of hydrogen, $C_1$-$C_6$ alkyl, $C_5$-$C_6$ cycloalkyl, $C_6$-$C_9$ cycloalkylalkyl and aryl or $R_2$ and $R_3$, taken together with the nitrogen atom to which they are linked, form a pentatomic or hexatomic saturated heteromonocyclic ring, optionally containing at least one additional heteroatom selected from oxygen and nitrogen; and the symbol (≔) represents a single or a double bond provided that when it is a double bond the hydrogen in the $5\alpha$ position doesn't exist and the pharmaceutically acceptable salts thereof.

In view of their $5$-$\alpha$ reductase inhibiting activity the compounds of the invention can be useful for the treatment of androgen dependent conditions.

6 Claims, No Drawings

UNSATURATED 17β-SUBSITUTED 3-CARBOXY STEROIDS

The present invention relates to new derivatives of unsaturated 17β-substituted 3-carboxy steroids, to a process for their preparation, to pharmaceutical compositions containing them and to the use of said compounds as inhibitors of androgen action, by means of testosterone 5α-reductase inhibition.

In certain androgen responsive tissues the action of testosterone is mediated primarily through its 5α-reduced metabolite, dihydrotestosterone (DHT) (Bruchowsky N., Wilson J. D.; J. Biol. Chem. 243, 5953, 1968). The conversion of testosterone to dihydrotestosterone is catalyzed by the enzyme 5α-reductase and if 5α-reductase is inhibited, the formation of dihydrotestosterone is reduced and its specific androgenic effect is attenuated or prevented.

The 5α-reductase inhibitors may find medical application for the treatment of hyperandrogenic conditions, e.g. certain prostatic diseases, such as benign prostatic hyperplasia and prostatic cancer, and certain skin-hair conditions, such as acne, seborrhoea, female hirsutism and male pattern baldness (Siiteri P. K., Wilson J. D., J. Clin. Invest. 49, 1737, 1970; Price V. H., Arch. Dermatol. III, 1496, 1975; Sandberg A. A., Urology 17, 34, 1981). Also breast cancer treatment can take advantage from use of 5α-reductase inhibitors as the said tumor is known to be aggravated by presence of androgens. Androst-4-en-3-one-17β-carboxylic acid and its methyl ester (Voigt and Hsia, Endocrinology, 92, 1216 (1973); Canadian Patent No. 970,692) are among the first steroidic compounds described as 5α-reductase inhibitors.

Two 5,10-secosteroids having a 3-keto-4,5-diene system in the expanded ring have been found to be selective inhibitors of rat epididymal 5α-reductase (Robaire et al., J. Steroid Biochem. 8, 307–310 (1977)).

(20R)-4-diazo-21-hydroxy-20-methyl-5α-pregnan-3-one and its analogs are reported to be enzyme activated inhibitors of testosterone 5α-reductase (Blohm et al., Biochem. Biophys. Res. Comm. 95, 273–80 (1980); U.S. Pat. No. 4,317,817).

Another series of enzyme-directed irreversible inhibitors of 5α-reductase have been prepared by introducing a 6-methylene moiety into substrates type 3-keto-4-progestins and androgens (Petrow et al., Steroids 38, 352–53 (1981); U.S. Pat. No. 4,396,615)).

More recently 4-aza-steroids have also been reported as inhibitors of steroid 5α-reductase (Liang et al., J. Steroid. Biochem. 19, 385–90 (1983); U.S. Pat. No. 4,377,584 and published European Patent Application no. 155,096).

In the end, unsaturated derivatives of 3-carboxy steroids have been reported as uncompetitive 5═-reductase inhibitors versus testosterone (Biorg. Chem. 17, 372–376 (1989); Eur. Pat. Appln. no. 0289327).

The present invention provides novel derivatives of unsaturated 17β-substituted 3-carboxy steroids of the following formula (I):

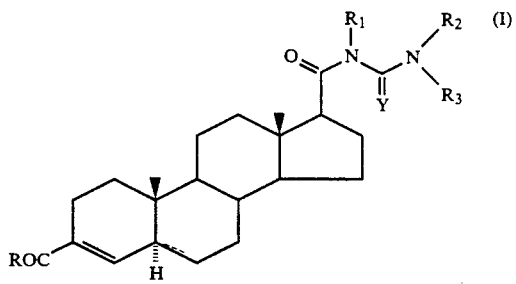

wherein
Y is oxygen or sulphur;
R is a group
  a) —OR$_4$, wherein R$_4$ is hydrogen or a C$_1$–C$_6$ alkyl group; or
  b)

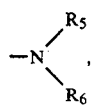

wherein each of R$_5$ and R$_6$, independently, is hydrogen or a C$_2$–C$_6$ alkyl group; or
  c)

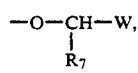

wherein R$_7$ is hydrogen or a C$_1$–C$_6$ alkyl group and W is a group
  i)

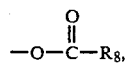

wherein R$_8$ is a C$_1$–C$_6$ alkyl group, a C$_5$–C$_6$ cycloalkyl group, a C$_6$–C$_9$ cycloalkylalkyl group, a phenyl group or a benzyl group;
  ii)

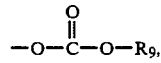

wherein R$_9$ is a C$_1$–C$_6$ alkyl group or a C$_5$–C$_6$ cycloalkyl group; or
  (iii)

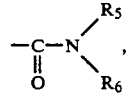

wherein R$_5$ and R$_6$ are as defined above; or
  d)

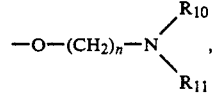

wherein each of R$_{10}$ and R$_{11}$ is, independently, hydrogen or a $C_1$-$C_6$ alkyl group or taken together with the nitrogen atom to which they are linked form a pentatomic or hexatomic saturated heteromonocyclic ring, optionally containing at least one additional heteroatom selected from oxygen and nitrogen, and n is an integer of 2 to 4;

$R_1$ is hydrogen, a $C_1$-$C_6$ alkyl group, a $C_5$-$C_6$ cycloalkyl group, a $C_6$-$C_9$ cycooalkyalkyl group or an aryl group;

each of $R_2$ and $R_3$ is, independently, selected from the group consisting of hydrogen, $C_1$-$C_6$ alkyl, $C_5$-$C_6$ cycloalkyl, $C_6$-$C_9$ cycloalkylalkyl and aryl or $R_2$ and $R_3$, taken together with the nitrogen atom to which they are linked, form a pentatomic or hexatomic saturated heteromonocyclic ring, optionally containing at least one additional heteroatom selected from oxygen and nitrogen; and the symbol (═) represents a single or a double bond provided that when it is a double bond the hydrogen in the 5α position doesn't exist.

In the formulae of this specification the dotted line (ııııı) indicates a substituent in the α configuration, i.e. below the plane of the ring, and the wedged line (◂) indicates a substituent in the β- configuration, i.e. above the plane of the ring.

The invention includes also the pharmaceutically acceptable salts of the compounds of formula (I) as well as all the possible isomers of formula (I) and their mixtures.

Also the metabolites and the metabolic precursors of the compounds of formula (I) are within the scope of the present invention.

In this specification the alkyl groups and the alkyl moiety of the cycloalkylalkyl groups may be straight or branched chain.

A $C_1$-$C_6$ alkyl group may be, for example, methyl, ethyl, isopropyl, n-butyl, tert-butyl or tert-butylmethyl (i.e. neopentyl).

A $C_5$-$C_6$ cycloalkyl group is cyclopentyl or cyclohexyl, preferably cyclohexyl.

A $C_6$-$C_9$ cycloalkylalkyl group may be, for example, cyclohexylmethyl.

An aryl group may be, for example, phenyl or benzyl.

When R is a group-$OR_4$ as defined above, preferably $R_4$ is hydrogen, methyl or ethyl, most preferably hydrogen; when R is a group

as defined above, preferably each of $R_5$ and $R_6$ is, independently, methyl or ethyl.

When R is a group

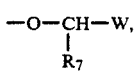

$R_7$ is preferably hydrogen or methyl.
When W is a group

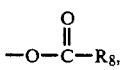

$R_8$ is preferably methyl, ethyl, propyl, n-butyl, t-butyl, cyclohexylmethyl, phenyl or benzyl.

When W is a group

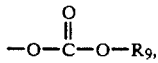

$R_9$ is preferably methyl, ethyl, i-propyl or cyclohexyl.
When W is a group

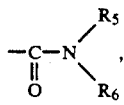

preferably each of $R_5$ and $R_6$ is, independently, methyl or ethyl.
When R is a group

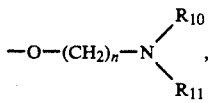

preferably each of $R_{10}$ and $R_{11}$ is, independently, hydrogen, methyl, ethyl, propyl, isopropyl or when $R_{10}$ and $R_{11}$ taken together with the nitrogen atom to which they are linked, form a pentatomic or hexatomic saturated heteromonocyclic ring as defined above, the group

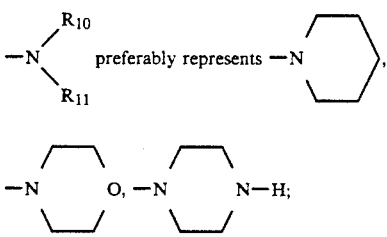

n is preferably 2,3.

$R_1$ is, preferably, methyl, ethyl, isopropyl, tert-butyl, cyclohexyl or cyclohexylmethyl.

Preferably each of $R_2$ and $R_3$ is, independently, hydrogen, methyl, ethyl, isopropyl, tert-butyl, cyclohexyl, cyclohexylmethyl, phenyl or when $R_2$ and $R_3$, taken together with the nitrogen atom to which they are linked, form a pentatomic or hexatomic saturated heteromonocyclic ring as defined above, the

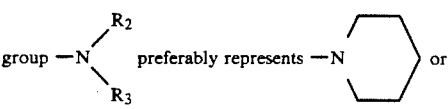

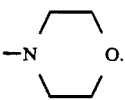

Pharmaceutically acceptable salts of the compounds of the invention are salts with pharmaceutically acceptable bases, either inorganic bases such as, for instance, alkali metal, e.g. sodium or potassium, or alkaline-earth metal, e.g. calcium or magnesium, or zinc or aluminium, hydroxides, or organic bases, such as, e.g., aliphatic amines as, e.g., methylamine, diethylamine, trimethylamine, ethylamine, and heterocyclic amines as, e.g., piperidine.

A preferred class of compounds according to the invention are the compounds of formula (I) wherein:
Y is oxygen or sulphur;
R is —OH, —OCH$_3$, —O CH$_2$CH$_3$,

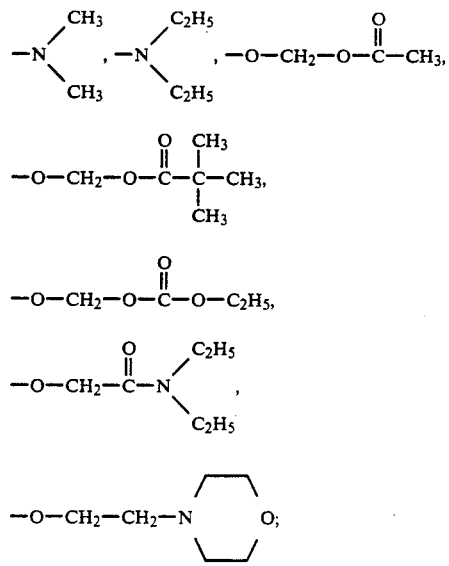

R$_1$ is methyl, ethyl, isopropyl, tert-butyl, cyclohexyl;

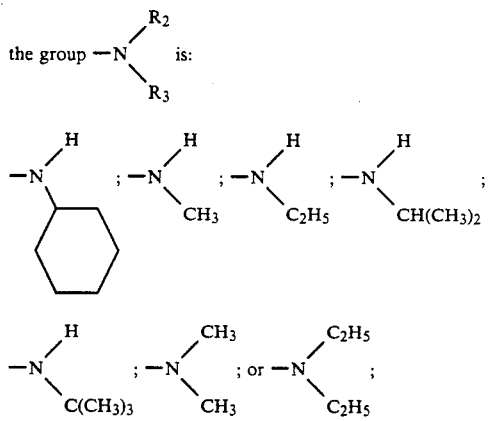

the symbol === represents a single or double bond, and the pharmaceutically acceptable salts thereof. Examples of specific compounds preferred under this invention are:

17β-[N-isopropyl-N-(N-isopropylcarbamoyl)carbamoyl]androsta-3,5-diene-3-carboxylic acid;
17β-[N-cyclohexyl-N-(N-cyclohexylcarbamoyl)carbamoyl]androsta-3,5-diene-3-carboxylic acid;
17β-[N-tert-butyl-N-(N-tert-butylcarbamoyl)carbamoyl]androsta-3,5-diene-3-carboxylic acid;
17β-[N-isopropyl-N-(N-isopropylthiocarbamoyl)carbamoyl]androsta-3,5-diene-3-carboxylic acid;
17β-[N-cyclohexyl-N-(N-cyclohexylthiocarbamoyl)carbamoyl]androsta-3,5-diene-3-carboxylic acid;
17β-[N-methyl-N-(N,N-diethylcarbamoyl)carbamoyl]androsta-3,5-diene-3-carboxylic acid;
methyl 17β-[N-isopropyl-N-(N-isopropylcarbamoyl)carbamoyl]androsta-3,5-diene-3-carboxylate;
methyl 17β-[N-isopropyl-N-(N-isopropylthiocarbamoyl)carbamoyl]androsta-3,5-diene-3-carboxylate;
methyl 17β-[N-cyclohexyl-N-(N-cyclohexylcarbamoyl)carbamoyl]androsta-3,5-diene-3-carboxylate;
methyl 17β-[N-cyclohexyl-N-(N-cyclohexylthiocarbamoyl)carbamoyl]androsta-3,5-diene-3-carboxylate;
methyl 17β-[N-tert-butyl-N-(N-tert-butylcarbamoyl)carbamoyl]androsta-3,5-diene-3-carboxylate;
methyl 17β-[N-methyl-N-(N,N-diethylcarbamoyl)carbamoyl]androsta-3,5-diene-3-carboxylate;
N,N-diethyl 17β-[N-isopropyl-N-(N-isopropylcarbamoyl)carbamoyl]androsta-3,5-diene-3-carboxamide;
N,N-diethyl 17β-[N-isopropyl-N-(N-isopropylthiocarbamoyl)carbamoyl]androsta-3,5-diene-3-carboxamide;
N,N-diethyl 17β-[N-cyclohexyl-N-(N-cyclohexylcarbamoyl)carbamoyl]androsta-3,5-diene-3-carboxamide;
N,N-diethyl 17β-[N-cyclohexyl-N-(N-cyclohexylthiocarbamoyl)carbamoyl]androsta-3,5-diene-3-carboxamide;
N,N-diethyl 17β-[N-methyl-N-(N,N-diethylcarbamoyl)carbamoyl]androsta-3,5-diene-3-carboxamide;
Acetyloxymethyl 17β-[N-isopropyl-N-(N-isopropylcarbamoyl)carbamoyl]androsta-3,5-diene-3-carboxylate;
Pivaloyloxymethyl 17β-[N-isopropyl-N-(N-isopropylcarbamoyl)carbamoyl]androsta-3,5-diene-3-carboxylate;
Ethoxycarbonyloxymethyl 17β-[N-isopropyl-N-(N-isopropylcarbamoyl)carbamoyl]androsta-3,5-diene-3-carboxylate;
(N,N-diethylcarbamoyl)methyl 17β-[N-isopropyl-N-(N-isopropylcarbamoyl)carbamoyl]androsta-3,5-diene-3-carboxylate;
2-(N-morpholino)ethyl 17β-[N-isopropyl-N-(N-isopropylcarbamoyl)carbamoyl]androsta-3,5-diene-3-carboxylate;

and, where appropriate, the pharmaceutically acceptable salts thereof.

A compound of formula (I) may be obtained by a process comprising
A) reacting a compound of formula (II)

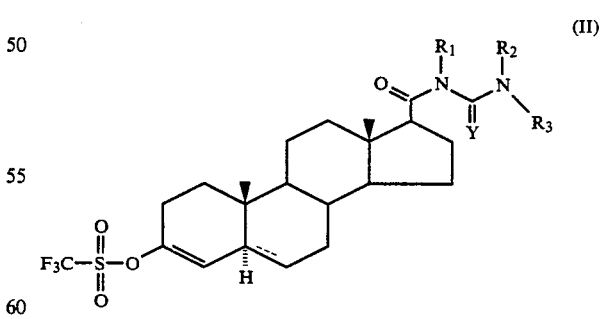

wherein the symbol === is a single or a double bond and Y, R$_1$, R$_2$, R$_3$ are as defined above, with carbon monoxide (CO) in the presence of a C$_1$–C$_6$ alkyl alcohol, so obtaining a compound of formula (I), wherein the symbol === is a single or a double bond, Y, R$_1$, R$_2$, R$_3$ are as defined above and R is a group OR$_4$ wherein R$_4$ is a C$_1$–C$_6$ alkyl group; or B) reacting a compound of formula (II) as defined above, with carbon monoxide in the presence of an amine of formula (III)

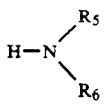     (III)

wherein $R_5$ and $R_6$ are as defined above so obtaining a compound of formula (I), wherein the symbol ═══ is a single or a double bond, Y, $R_1$, $R_2$, $R_3$ are as defined above and R is a group

wherein $R_5$ and $R_6$ are as defined above; or reacting a compound of formula (I), wherein the symbol ═══ is a single or a double bond, Y, $R_1$, $R_2$, $R_3$ are as defined above and R is a group $OR_4$, wherein $R_4$ is hydrogen, with a compound of formula (IV)

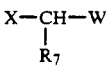     (IV)

wherein $R_7$ and W are as defined above and X is a halogen atom, so obtaining a compound of formula (I), wherein the symbol ═══ is a single or a double bond, Y, $R_1$, $R_2$, $R_3$ are as defined above and R is a group

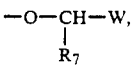

wherein $R_7$ and W are as defined above; or

D) reacting a compound of formula (I), wherein the symbol ═══ is a single or a double bond, Y, $R_1$, $R_2$, $R_3$ are as defined above and R is a group $OR_4$ wherein $R_4$ is hydrogen, with a compound of formula (V)

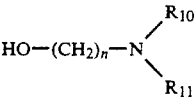     (V)

wherein $R_{10}$ and $R_{11}$ are as defined above, so obtaining a compound of formula (I), wherein the symbol ═══ is a single or a double bond, Y, $R_1$, $R_2$, $R_3$ are as defined above and the group R is a group

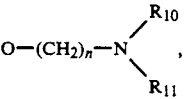

wherein n, $R_{10}$ and $R_{11}$ are as defined above; and, if desired, converting a compound of formula (I), wherein the symbol ═══ is a single or a double bond, Y, $R_1$, $R_2$, $R_3$ are as defined above and R is a group $OR_4$, wherein $R_4$ is a $C_1$–$C_4$ alkyl group, by selective hydrolysis, into a corresponding compound of formula (I) wherein the symbol ═══ is a single or a double bond, Y, $R_1$, $R_2$, $R_3$ are as defined above and R is a group $OR_4$ wherein $R_4$ is hydrogen, and/or, if desired, converting a compound of formula (I) into a salt thereof, or, converting a salt of a compound of formula (I) into the corresponding free compound, and/or, if desired, separating a mixture of isomers of a compound of formula (I) into the single isomers.

The reaction of a compound of formula (II) with carbon monoxide in the presence of a $C_1$–$C_6$ alkyl alcohol, according to the process variant A may be carried out, e.g., by treating a solution of the compound of formula (II) in a suitable organic solvent, preferably dimethylformamide (DMF), with an organic base such as, for example, triethylamine (TEA), a palladium complex such as, for example, bis (triphenylphosphine) palladium (II) acetate or bis (triphenylphosphine) palladium (II) chloride, and a $C_1$–$C_6$ alkyl alcohol.

Optionally the palladium complexes, can be formed in situ, by adding, separately, a phosphine, such as triphenylphosphine, and a palladium salt, such as, for example, palladium (II) acetate or palladium (II) chloride.

Then the reaction mixture is purged with carbon monoxide (CO) for some minutes and then stirred under a CO balloon for a time varying from one hour to 48 hours, at a temperature ranging from 0° C. to 40° C. Analogous procedure is described, e.g., in Tetr. Lett. 26 (8), 1109–12, (1985).

The reaction of a compound of formula (II) with carbon monoxide and an amine of formula (III), according to the process variant B), may be carried out following the same procedure reported above wherein, instead of an alkyl alcohol, an amine of formula (III) is used.

The halogen atom X in the compound of formula (IV) and (V) is preferably chlorine, bromine, iodine, most preferably chlorine or bromine.

The reaction of a compound of formula (I) with a compound of formula (IV), according to the process variant C), may be carried out in a solvent such as, for example, dimethylformamide, dimethylacetamide, acetonitrile, in the presence of a base such as, for example, an alkali metal hydride, preferably sodium hydride, or an alkali metal alkoxide, preferably sodium methoxide, sodium ethoxide, potassium tert-butoxide, or an amine, preferably pyridine or triethylamine, optionally, wnen X is not iodine, in the presence of an alkali metal iodide, preferably sodium iodide, at a temperature ranging from about 0° C. to about room temperature, for a time varying from about, for example, 2 hours to about 24 hours, preferably under an inert atmosphere of, for example, nitrogen.

The reaction of a compound of formula (I) with a compound of formula (V), according to the process variant D), may be carried out in a solvent such as, for example, ethyl acetate, dimethylformamide, dimethylacetamide, acetonitrile, in the presence of a base such as, for example, an alkali metal hydride, preferably sodium hydride, or an alkali metal alkoxide, preferably sodium methoxide, sodium ethoxide, potassium tert-butoxide, or an amine, preferably pyridine or triethylamine, optionally, when X is not iodine, in the presence of an alkali metal iodide, preferably sodium iodide, at a temperature ranging from about 0° C. to about 80° C., for a time varying, for example, from one hour to eight hours.

The conversion of a compound of formula (I), wherein the symbol ═══ is a single or a double bond, Y, $R_1$, $R_2$, $R_3$ are as defined above and R is a group $OR_4$ wherein $R_4$ is a $C_1$–$C_6$ alkyl group, into a corresponding compound of formula (I), wherein the symbol === is a single or a double bond, Y, $R_1$, $R_2$, $R_3$ are as defined above and R is a group $OR_4$ wherein $R_4$ is hydrogen may be carried out, e.g., in a suitable solvent, such as, for example, methanol, ethanol, tetrahydrofurane, dioxane, in the presence of an aqueous concentrate solution of an alkali metal hydroxide such as, for example, potassium hydroxide, sodium hydroxide or, preferably, lithium hydroxide, for a time varying from some hours to some days, at a temperature ranging from about 0° C. to the reflux temperature of the solvent, optionally under an inert atmosphere of nitrogen.

Standard procedures may be used for converting a compound of formula (I) into a pharmaceutically acceptable salt thereof as well as for obtaining a free compound from the corresponding salt and for separating a mixture of isomers of formula (I) into the single isomers.

A compound of formula (II) wherein the symbol === is a single bond and Y, $R_1$, $R_2$, $R_3$ are as defined above, may be obtained from a compound of formula (VI)

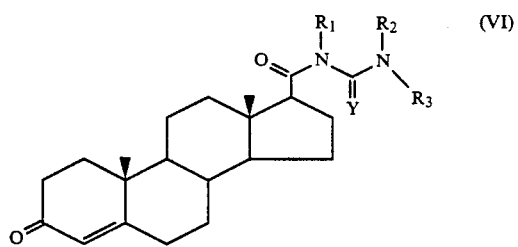

wherein Y, $R_1$, $R_2$ and $R_3$ are as defined above according to the following procedure.

A compound of formula (VI) is dissolved in a suitable organic solvent such as, for example, tetrahydrofurane (THF), in the presence of a suitable organic proton donor, such as, for example, tert-butanol or aniline; then a reducing metal amine solution, e.g. a lithium/liquid ammonia solution, is added to the obtained mixture and then the reaction mixture is stirred at a temperature ranging from about −100° C. to about −30° C., preferably at about −78° C., for a time of about 2 or 3 hours. Then the reaction is quenched with an organic lithium scavenger, such as, for example, bromobenzene, dibromoetane or, preferably, isoprene and the solvent is removed in vacuo.

The solid residue is redissolved in an organic solvent such as, for example, tetrahydrofurane or diethyl ether, and treated with an N-aryltrifluoroalkylsulfonimide, preferably with N-phenyltrifluoromethylsulfonimide, at a temperature ranging from about −20° C. to about −30° C., for a time varying from about 2 hours to about 24 hours.

The method is reported, e.g., in Tetr.Lett, 1983, 24, 979-982. A compound of formula (II), wherein the symbol === is a double bond and Y, $R_1$, $R_2$, $R_3$ are as defined above, may be obtained from a corresponding compound of formula (VI), wherein $R_1$, $R_2$ and $R_3$ are as defined above and === is a single bond, e.g. by adding to a solution containing a compound of formula (VI), as defined above, and an organic hindered base such as, 2,6-di-tert-butyl-4-methylpyridine, in a suitable organic solvent such as, e.g., methylene chloride, a trifluorosulphonic anhydride, preferably trifluoromethanesulfphonic anhydride, according to the procedure reported in Synthesis 438-440, 1979.

The compounds of formula (VI) can be in their turn synthesized using known procedures, for instance according to the three pathways a), b) and c) reported in the scheme depicted herebelow.

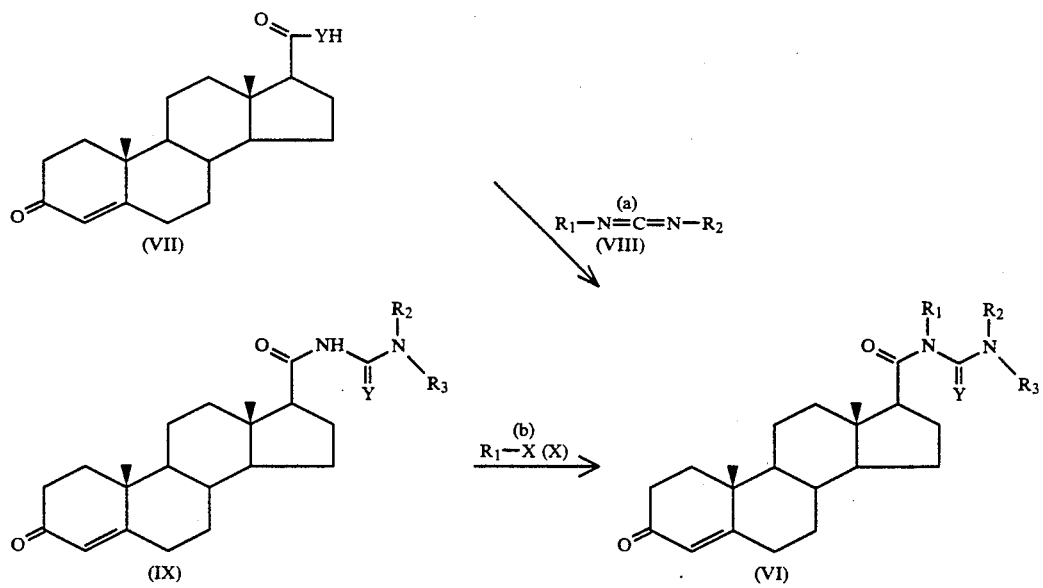

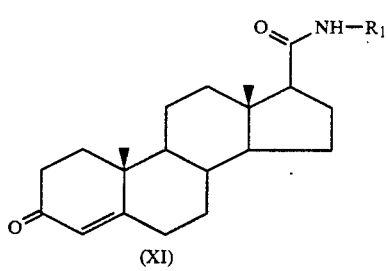

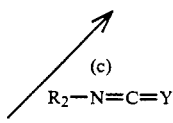

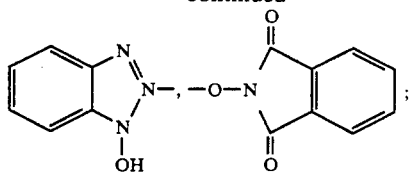

According to reaction (a), a compound of formula (VI) wherein Y, $R_1$, $R_2$ and $R_3$ are as defined above, provided that $R_1$ and $R_2$ are not hydrogen and $R_3$ is hydrogen, may be obtained reacting a compound of formula (VII), wherein Y is as defined above, with a carbodiimmide of formula (VIII) wherein $R_1$ and $R_2$ are as defined above.

According to reaction (b), a compound of formula (VI), wherein $R_1$ is as defined above, provided that it is not hydrogen, and Y, $R_2$ and $R_3$ are as defined above, may be obtained from a compound of formula (IX), wherein $R_2$ and $R_3$ are as defined above, by alkylation with a compound of formula (X) wherein $R_1$ is as defined above provided that it is not hydrogen, and X is a halogen atom, e.g., iodine.

According to reaction (c), a compound of formula (VI), wherein $R_3$ is hydrogen and Y, $R_1$, $R_2$ are as defined above, provided that $R_2$ is not hydrogen, may be obtained from a compound of formula (XI), wherein $R_1$ is as defined above, by reaction with a compound of formula (XII) wherein $R_2$ and Y are as defined above, provided that $R_2$ is not hydrogen.

Compounds of formula (VII), wherein Y=S, formula (IX) and formula (XI) may be obtained reacting a compound of formula (XIII)

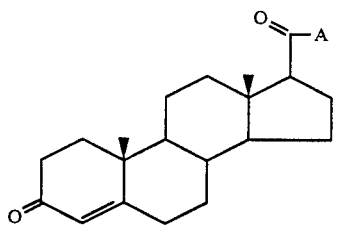

wherein A may be any suitable activating group of the carboxy function which is useful in the formation of amidic and peptidic linkages with the appropriate reagent as indicated in the following. The suitable activating group may be, for instance, one of the following groups:

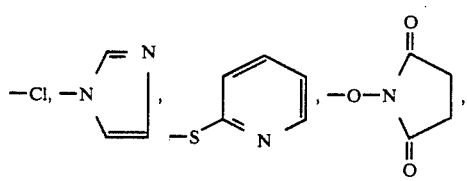

In particular, the compounds of formula (VII) wherein Y is sulfur, may be, e.g., obtained from compounds of formula (XIII) according to known procedures.

One procedure may involve, for example, reacting a compound of formula (XIII) wherein A is chlorine, with gaseous hydrogen sulfide in the presence of dimethylthioformamide, in a solvent such as, for example, $CH_2Cl_2$, at room temperature for a time varying from, e.g., ten minutes to some hours under vigorous stirring, according to the method described in Synthesis, 671-2 (1985).

Another procedure may involve, e.g., reacting a compound of formula (XIII) wherein A is $$-S\underset{N}{\diagdown}$$

that is the S-2-pyridylthioate derivative, with an excess of sodium hydrogen sulfide monohydrate. The reaction may be performed in a solvent such as, for example, methylene chloride, tetrahydrofurane, acetonitrile, at a temperature ranging from, e.g., about 0° C. to about 50° C., for a time varying, e.g., from about one hour to about 48 hours.

A compound of formula (VII) wherein Y is sulphur may also be synthetized according to the general methods described in the literature for the synthesis of thiocarboxylic acids, for example in analogous way as described in Houben Weyl, Bd E 5, pages 832-842, or by Duns F. in Barton and Ollis, Comprehensive Organic chemistry, Vol. 3 Pergamon Press, Oxford, 1979, pages 20-32.

A compound of formula (IX), as defined above, may be obtained reacting a compound of formula (XIII), as defined above, with an urea of formula (XIV),

wherein $R_2$ and $R_3$, as as defined above.

A compound of formula (XI), may be obtained reacting a compound of formula (XIII), with an amine of formula (XV)

$$R_1-NH_2 \quad (XV)$$

wherein $R_1$ is as defined above.

A compound of formula (XIII) may be obtained from a compound of formula (VII) wherein Y is oxygen by well known procedures. The compounds of formulae (III), (IV), (V), (VII), wherein Y is oxygen, (VIII), (X), (XII), (XIV) and (XV) are commercially available compounds or can be prepared by known procedures from known compounds.

The compounds of the present invention inhibit specifically the testosterone 5α-reductase enzyme and, therefore, can be useful for the treatment of androgen-dependent conditions.

For example, the inhibitory effect of the compounds of the invention on 5α-reductase was determined in vitro, according to the test procedure reported herebelow.

Inhibition of 5α-reductase was evaluated using the particulate fraction (containing nuclei, microsomes and mitochondria) from homogenates of human benign prostatic hypertrophyc tissue as the enzyme source.

The particulate fraction was prepared centrifuging prostate homogenate at 140,000 × g.

The resulting pellet, washed several times, was resuspended in buffer and stored at −80° C. in aliquots containing 10 mg protein/ml.

The assay for 5α-reductase was done in a final volume of 0.5 ml, containing 1 mM dithiothreitol, 40 mM TRIS-HCl buffer pH 5.5, 5 mM NADPH, 1 μM [4-$^{14}$C]testosterone, 0.3 mg protein of the prostate particulate fraction and various concentrations of the inhibitors. After 30 min incubation at 37° C. the reaction was terminated by addition of 2.0 ml diethyl ether and the organic phase was separated, evaporated under $N_2$ and resuspended in ethyl acetate. Testosterone metabolites in this extract were separated in TLC on silica gel F 254 plates (Merck) using chloroform, acetone and n-hexane (2:1:2) as developing solvent system. Radioactivity on the plate was scanned and analyzed from quantitative plots printed by a TLC-analizer (Berthold). The fractional 5α-reduction of testosterone was calculated by relating the $^{14}$C-radioactivity in the 5α-reduced metabolites 5α-dihydrotestosterone, 3α- and 3β-androstanediols) regions to the total radioactivity in the testosterone and 5α-reduced metabolites regions.

The concentration of each compound required to reduce control 5α-reductase by 50%($IC_{50}$) was determined by plotting % inhibition versus log of inhibitor concentration.

Thus, for example in the above test, a representative compound of the invention, namely 17β-[N-isopropyl-N-(N-isopropylcarbamoyl)carbamoyl]androst-3,5-diene-3-carboxylic acid was found to produce 50% inhibition on human prostatic 5α-reductase at the dose of 3nM.

In view of the before indicated activity the compounds of the invention can be therapeutically useful in the situations in which a decrease in androgen action, by means of 5α-reductase inhibition, is desirable such as, for example, benign prostatic hyperplasia, prostatic and breast cancers and certain skin-hair conditions such as, e.g., acne, seborrhoea, female hirsutism and male pattern baldness.

They are useful both in the pharmaceutical field and, e.g. for the treatment of prostatic hyperplasia, in the veterinary field.

The toxicity of the compounds of the invention is quite negligible so that they can be safely used in therapy.

The compounds of the invention can be administered in a variety of dosage forms, e.g. orally, in the form of tablets, capsules, sugar or film coated tablets, liquid solutions or suspensions; rectally, in the form of suppositories; parenterally, e.g. intramuscularly, or by intravenous injection or infusion; topically, e.g. in the form of creams.

The dosage depends on the age, weight, conditions of the patient and administration route; for example the dosage adopted for oral administration to adult humans may range from about 0.2 to about 100 mg pro dose, from 1 to 3 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administerd in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing granulating, tabletting, sugar-coating, or film-coating processes.

The liquid dispersions for oral administration may be, e.g., syrups, emulsions and suspensions.

The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycol, e.g. propylene glycol and if desired, a suitable amount of lidocaine hydrochloride.

The solutions for intravenous injections of infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant of lecithin.

Conventional carriers may be used for topical formulations. The terms "pharmaceutical" and the like as used in the present specification are meant to include also the meanings "veterinary and the like".

The following examples illustrate but do not limit the invention.

EXAMPLE 1

1-(3-oxoandrost-4-ene-17β-carbonyl)-1,3-diisopropylurea (VI): Y=O, $R_1$=iPr, $R_2$=iPr, $R_3$=H]

To a stirred solution of androst-4-en-3-one-17β-carboxylic acid (50 g) in ethylacetate (1.5 l) and triethylamine (33 ml) N,N-diisopropylcarbodiimide (32.4 ml) is added dropwise during 5 minutes and then the reaction mixture is refluxed for 1 h.

The reaction mixture is cooled and filtered on buckner; the filtrate is washed with 1N HCl, 0.5N NaHCO$_3$, brine and anhydrified over sodium sulphate and concentrated to about 150 ml; by cooling the title product precipitates and it is filtered by suction filtration, washed with isopropylic ether so affording 54 g of white crystalline compound (m.p. 172°-175° C.), $[\alpha]_D$ +89° (c=1, DMF).

Following an analogous procedure the below listed compounds can be prepared:

1-(3-oxoandrost-4-ene-17β-carbonyl)-1,3-dicyclohexylurea (m.p. 178°-180° C.), $[\alpha]_D$ +77° (c=1, DMF) and 1-(3-oxoandrost-4-ene-17β-carbonyl)-1,3-ditertbutylurea (m.p. 175°-177° C.), $[\alpha]_D$ +53° (c=0.5, DMF).

EXAMPLE 2

1-(3-oxoandrost-4-ene-17β-carbonyl)-1,3-diisopropylthiourea [(VI): Y=S, $R_1$=iPr, $R_2$=iPr]

A solution of 2-pyridyl 3-oxoandrost-4-ene-17β-carbothioate

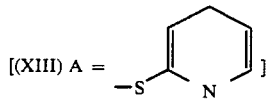

[(XIII) A = ]

(3.0 g) in tetrahydrofurane (70 ml) is treated with 70% sodium hydrogen sulphide monohydrate (3.9 g) and the mixture is heated under reflux for 2 hours.

After acidification with 1N hydrochloric acid, the mixture is extracted thoroughly with methylene chloride.

The combined organic extracts are washed with water till neutrality, dried over sodium sulphate and evaporated to dryness.

Further purification by flash chromatography on silica gel (eluant: methylene chloride/acetone 95:5) affords 3.5 g of 3-oxoandrost-4-ene-17β-carbothioic acid [(VII) Y=S].

NMR (CDCl$_3$) δ: 5.70 (s, 1H, H(4)), 1.2 (s, 3H, CH$_3$(19)), 0.75 (s, 3H, CH$_3$(18)).

MS (m/z): 332 M+− 299 M— −SH⁻ +(100%) 271 M— −COSH⁻ +

A solution of the thioacid so obtained (2.54 g) in ethyl acetate (59 ml) is treated first with triethylamine (1.6 ml) and then with N,N'-diisopropylcarbodiimide (1.54 ml) and the mixture is stirred for 5 hours at room temperature.

The reaction mixture is directly chromatographed on a column of silica gel, eluting with methylene chloride-/ethyl acetate 90:10, so obtaining the title compound (2.03 g, recrystallized from methylene chloride/ethyl acetate; m.p. 180°-183° C.), $[\alpha]_D$ +146° (c=1, DMF).

NMR (CDCl$_3$) δ: 6.8 (d, 1H, NH), 5.75 (s, 1H, H(4)), 4.2-4.8 (m, 2H, NH—CH(CH$_3$)$_2$), 1.3 (2d, 12H, 4 isopropylic CH$_3$), 1.2 (s, 3H, CH$_3$(19)), 0.85 (s, 3H, CH$_3$(18)).

MS (m/z): 458 M+− 357 M—S=C=N—CH(CH$_3$)$_2$⁻ +. 299 357— −NH—CH(CH$_3$)$_2$⁻ + (100%)

Following an analogous procedure, the compounds listed below can be obtained:

1-(3-oxoandrost-4-ene-17β-carbonyl)-1,3-dicyclohexylthiourea (m.p. 209°-212° C.) and 1-(3-oxoandrost-4-ene-17β-carbonyl)-1,3-ditertbutylthiourea.

EXAMPLE 3

3-{[(trifluoromethyl)sulfonyl]oxy}-17β-[N-isopropyl-N-(N-isopropylcarbamoyl)carbamoyl]androsta-3,5-diene [(II) Y=O, $R_1$=iPr, $R_2$=iPr, $R_3$=H, ═ double bond]

To a stirred solution of 17β-[N-isopropyl-N-(N-isopropylcarbamoyl)carbamoyl]androst-4-en-3-one (6.0 g) and 2,6-ditert-butyl-4-methylpyridine (3.63 g) in methylene chloride (54 ml), maintained under inert atmosphere of nitrogen at room temperature, the trifluoroacetic anhydride (2.54 ml) is added dropwise during 10 minutes.

After stirring for 30 minutes, the reaction mixture is diluted with methylene chloride and washed with saturated aqueous sodium bicarbonate, with 1N HCl, with water until neutrality and anhydrified over sodium sulphate.

The foam which is obtained is purified by flash chromatography on silica gel (eluent: n-hexane/ethylacetate 75:25), so obtaining 4.6 g of the title compound (m.p. 135°-140° C.).

NMR (CDCl$_3$) δ: 5.80 (m, 1H, H(4)), 5.45 (m, 1H, H(6))

MS (m/z): 574 M+−, 489 M— O=C=N—CH(CH$_3$)$_2$⁻ +−, 474 489— −CH$_3$⁻ +, 403 489 — −CO—NH—CH(CH$_3$)$_2$⁻ +, 356 489— −SO$_2$CF$_3$⁻ + (100%)

Following an analogous procedure the below listed compounds can be prepared:

3-{[(trifluoromethyl)sulfonyl]oxy}-17β-[N-isopropyl-N-(N-isopropylthiocarbamoyl)carbamoyl]androsta-3,5-diene;

3-{[(trifluoromethyl)sulfonyl]oxy}-17β-[N-cyclohexyl-N-(N-cyclohexylcarbamoyl)carbamoyl]androsta-3,5-diene; (m.p. 140°-145° C.)

3-{[(trifluoromethyl)sulfonyl]oxy}-17β-[N-cyclohexyl-N-(N-cyclohexylthiocarbamoyl)carbamoyl]androsta-3,5-diene;

3-{[(trifluoromethyl)sulfonyl]oxy}-17β-[N-tert-butyl-N-tert-butylcarbamoyl)carbamoyl]androsta-3,5-diene; (m.p. 123°-124° C.) and 3-{[(trifluoromethyl)sulphonyl]oxy}-17β-[N-methyl-N-(N,N-diethylcarbamoyl)carbamoyl]androsta-3,5-diene.

EXAMPLE 4

Methyl 17β-[N-isopropyl-N-(N-isopropylcarbamoyl)carbamoyl]androsta-3,5-diene-3-carboxylate

[(I): Y=O, R$_1$=iPr, R$_2$=iPr, R$_3$=H, ═ double bond, R=OR$_4$, R$_4$=CH$_3$]

To a solution of 3-{[(trifluoromethyl)sulfonyl]oxy}-17β-[N-isopropyl-N-(N-isopropylcarbamoyl)carbamoyl]androsta-3,5-diene (4.6 g) in dimethylformamide (17 ml), methanol (17 ml) and triethylamine (2.23 ml) bis(triphenylphosphine) palladium (II) acetate (180 mg) is added; the mixture is purged with carbon monoxide for 5 minutes and then is stirred overnight at room temperature under a carbon monoxide atmosphere (maintained by means of a balloon).

Ethyl acetate is then added and the organic solution is washed with water until neutral, anhydrified over sodium sulphate and the solvent is removed under vacuum. The crude is purified by flash chromatography on silica gel (eluent n-hexane-ethylacetate 75:25) so obtaining 3.5 g of the title product (m.p. 150°–155° C.).

NMR (CDCl$_3$) δ: 7.05 (m, 1H, H(4)), 5.80 (m, 1H, H(6)), 3.75 (s, 3H, COOCH$_3$)

MS (m/z): 484 M$^{+-}$, 399 M— O=C—N—CH(CH$_3$)$_2$⁻ +—, 384 399— -CH$_3$⁻ +, 367 399—CH$_3$OH⁻ +—, 352 384—CH$_3$OH⁻ +.

Following an analogous procedure the below listed compounds can be prepared:

Methyl 17β-[N-isopropyl-N-(N-isopropylthiocarbamoyl)carbamoyl]androsta-3,5-diene-3-carboxylate;

Methyl 17β-[N-cyclohexyl-N-(N-cyclohexylcarbamoyl)carbamoyl]androsta-3,5-diene-3-carboxylate; (m.p. 168-170° C.)

Methyl 17β-[N-cyclohexyl-N-(N-cyclohexylthiocarbamoyl) carbamoyl]androsta-3,5-diene-3-carboxylate;

Methyl 17β-[N-tert-butyl-N-(N-tert-butylcarbamoyl)carbamoyl]androsta-3,5-diene-3-carboxylate; (m.p. 110°–115° C.) and Methyl 17β-[N-methyl-N-(N,N-diethylcarbamoyl)carbamoyl]androsta-3,5-diene-3-carboxylate.

EXAMPLE 5

17β-[N-isopropyl-N-(N-isopropylcarbamoyl)carbamoyl]androsta-3,5-diene-3-carboxylic acid [(I): Y=O, R$_1$=iPr, R$_2$=iPr, R$_3$=H, ═ double bond, R=OR$_4$, R$_4$=H]

A mixture of methyl 17β-[N-isopropyl-N-(N-isopropylcarbamoyl) carbamoyl]androsta-3,5-diene-3-carboxylate (3.29 g), methanol (136 ml) and aqueous lithium hydroxide (1.424 g in 36 ml of water) is stirred at room temperature for 5 days.

The methanol is evaporated under vacuum and water is added; the mixture is acidified with 1N HCl and extracted with methylene chloride; the organic layers are washed with brine, water until neutrality, anhydrified over sodium sulphate and the solvent removed under vacuum.

The yellow solid obtained is purified by flash chromatography on silica gel (eluent: methylene chloride/acetone 9:1) so obtaining 1.66 g. of a white solid, which is crystallized from methylene chloride/ethylacetate (1.15 g, m.p. 173°–175° C. dec.).

[α]$_D$ −132° (c=1, CHCl$_3$)

NMR (CDCl$_3$) δ: 7.13 (m, 1H, H(4)), 6.50 (bm, 1H, CONH), 5.82 (m, 1H, H(6)), 4.48 (m, 1H,

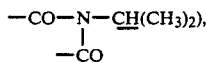

3.98 (m, 1H, CONH—CH(CH$_3$)$_2$), 2.69 (t, 1H, CH(17α)), 1.15-1.35 (4d- 12H, 4 isopropylic CH$_3$), 0.90 (s, 3H, CH$_3$(19)), 0.80 (s, 3H, CH$_3$(18)).

MS (m/z): 385 M— O=C=N—CH(CH$_3$)$_2$⁻ +— (100%) 370 385— -CH$_3$⁻ + 352 385— -CH$_3$—H$_2$O⁻ +

Following an analogous procedure the below listed compounds can be prepared:

17β-[N-isopropyl-N-(N-isopropylthiocarbamoyl)carbamoyl]androsta-3,5-diene-3-carboxylic acid (m.p. 125°–130° C.);

17β-[N-cyclohexyl-N-(N-cyclohexylcarbamoyl)carbamoyl]androsta-3,5-diene-3-carboxylic acid; (m.p. 253°–255° C., AcOEt); [α]$_D$ −110° (c=1, CHCl$_3$)

17β-[N-cyclohexyl-N-(N-cyclohexylthiocarbamoyl)carbamoyl]androsta-3,5-diene-3-carboxylic acid;

17β-[N-tert-butyl-N-(N-tert-butylcarbamoyl)carbamoyl]androsta-3,5-diene-3-carboxylic acid; (m.p. 118°–120° C.), [α] −134° (c=0.5, DMF) and 17β-[N-methyl-N-(N,N-diethylcarbamoyl)carbamoyl]androsta-3,5-diene-3-carboxylic acid.

EXAMPLE 6

N,N-diethylcarbamoyl 17β-[N-isopropyl-N-(N-isopropylcarbamoyl)carbamoyl]androsta-3,5-diene-3-carboxamide [(I): Y=O, R$_1$=iPr, R$_2$=iPr, R$_3$=H, ═ double bond,

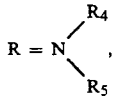

R$_4$=R$_5$=Et]

A mixture of 3-{[(trifluoromethyl)sulfonyl]oxy}-17β-[N-iso-propyl-N-(N-isopropylcarbamoyl)carbamoyl]androsta- 3,5-diene (574 mg), palladium acetate (6 mg), triphenylphosphine (16 mg) and diethylamine (4.2 ml) in dimethylformamide (4 ml) is purged with carbon monoxide for 10 minutes and then is stirred overnight at room temperature under a carbon monoxide atmosphere (mantained by means of a balloon).

Ethyl acetate is then added and the organic solution is washed with water until neutral, anhydrified over sodium sulphate and the solvent is removed under vacuum.

The crude is purified by flash chromatography on silica gel (eluent n-hexane-ethyl acetate 60/40) so obtaining 310 mg of the title compound.

Following an analogous procedure the below listed compounds can be prepared:

N,N-diethyl 17β-[N-isopropyl-N-(N-isopropylthio carbamoyl) carbamoyl]androsta-3,5-diene-3-carboxamide;

N,N-diethyl 17β-[N-cyclohexyl-N-(N-cyclohexylcarbamoyl) carbamoyl]androsta-3,5-diene-3-carboxamide;

N,N-diethyl 17β-[N-cyclohexyl-N-(N-cyclohexylthiocarbamoyl) carbamoyl]androsta-3,5-diene-3-carboxamide and N,N-diethyl 7β-[N-methyl-N-(N,N-diethylcarbamoyl)-carbamoyl]androsta-3,5-diene-3-carboxamide.

EXAMPLE 7

2-(N-morpholino)ethyl 17β-[N-isopropyl-N-(N-isopropylcarbamoyl)carbamoyl]androsta-3,5-diene-3-carboxylate [(I): Y=O, $R_1$=iPr, $R_2$=iPr, $R_3$=H, ═ double bond,

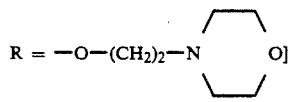

To a solution of 17β-[N-isopropyl-N-(N-isopropylcarbamoyl) carbamoyl]androsta-3,5-diene-3-carboxylic acid (235 mg) in methylene chloride (2.5 ml), 4-(2-hydroxyethyl)morpholine (7.4 μl) and 4-pyrrolidinopyridine (3.7 mg) are added slowly, followed by dicyclohexylcarbodiimide (124 mg). After some minutes the clear solution becomes cloudy. The stirring is continued at room temperature for 3 hours. The mixture is filtered on a paper-filter and the solid is washed with methylene chloride; the filtrate is evaporated to dryness. The crude oil so obtained (394 mg) is purified by flash chromatography on silica gel (eluant: methylene chloride/acetone 8:2) so obtaining 170 mg of the title compound.

NMR (CDCl3) δ: 7.00(m, 1H, H(4)), 6.50(bm, 1H, CONH), 5.78(m, 1H, H(6)), 4.48

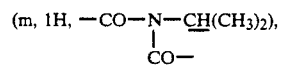

4.27(m, 2H, 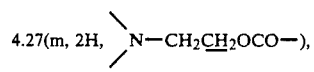), 3.98(m, 1H, CONHC$\underline{H}$(CH3)2), 3.68

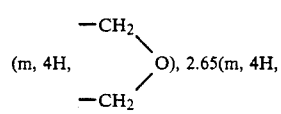

(m, 4H, ...O), 2.65(m, 4H,

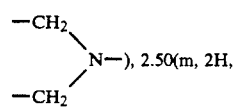

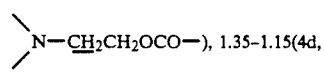, 2.50(m, 2H,

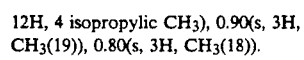, 1.35–1.15(4d, 12H, 4 isopropylic CH3), 0.90(s, 3H, CH3(19)), 0.80(s, 3H, CH3(18)).

MS (m/z): 583 M+−
498 M-O═C═N—CH(CH3)2]+−

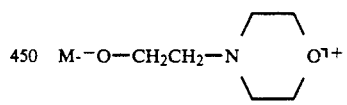

450 M-−O—CH2CH2—N

-continued

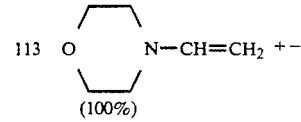

113 (100%)

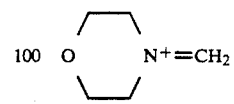

100

EXAMPLE 8

Acetyloxymethyl 17β-[N-isopropyl-N-(N-isopropylcarbamoyl)carbamoyl]androsta-3,5-diene-3-carboxylate [(I): Y=O, $R_1$=iPr, $R_2$=iPr, $R_3$=H, ═ double bond, R=—O—CH2O—COMe]

To a solution of 17β-[N-isopropyl-N-(N-isopropylcarbamoyl) carbamoyl]androsta-3,5-diene-3-carboxylic acid (500 mg) in anhydrous dimethylformamide (15 ml), maintained under nitrogen atmosphere and cooled to about 0° C. with an ice-bath, sodium hydride (47.8 mg of a 80% suspension in mineral oil) is added and the mixture is stirred at 0° C. for 1 hour. Bromomethylacetate (0.31 ml) is added dropwise and the solution is stirred at room temperature for 3 hours. Then the mixture is poured into ice-water and extracted with toluene (3×50 ml); the combined organic extracts are washed with water, with brine and anhydrified over sodium sulphate. The solvent is removed under vacuum, thus affording 500 mg of crude material that is purified by flash chromatography on silica gel (eluant: n-hexane/ethyl acetate 65:35) so obtaining 270 mg of the title compound as a white solid (m.p. 183°–185° C.).

Elemental analysis: calculated for $C_{31}H_{46}N_2O_6$ C 68.61 H 8.54 N 5.16 found C 68.34 H 8.76 N 5.08

NMR (CDCl3) δ: 7.05 (m, 1H, H(4)), 6.40 (bm, 1H, CONH), 5.80 (m, 1H, H(6)), 5.75 (s, 2H, CH3COOC$\underline{H}$2OCO—), 4.48

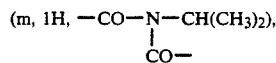

3.98 (m, 1H, —CONHC$\underline{H}$(CH3)2), 2.08 (s, 3H, CH3CO), 1.35–1.15 (4d, 12H, 4 isopropylic CH3), 0.90 (s, 3H, CH3(19)), 0.80 (s, 1H, CH3(18)).

MS (m/z): 542 M+− 457 M − O═C═N—CH(CH3)2]+− 367 M − O═C═N—CH(CH3)2 − CH3COOCH2OH]+− (100%) 352 367—−CH3]+

Following an analogous procedure and using the appropriate starting materials, the compounds listed below can be prepared: Pivaloyloxymethyl 17β-[N-isopropyl-N-(N-isopropylcarbamoyl) carbamoyl]androsta-3,5-diene-3-carboxylate and Ethoxycarbonyloxymethyl 17β-[N-isopropyl-N-(N-isopropylcarbamoyl)carbamoyl]androsta-3,5-diene-3-carboxylate. N,N-diethylcarbamoylmethyl 17β-[N-isopropyl-N-(N-isopropylcarbamoyl)carbamoyl]androsta-3,5-diene-3-carboxylate.

EXAMPLE 9

N,N-diethylcarbamoylmethyl 17β-[N-isopropyl-N-(N-isopropylcarbamoyl)carbamoyl]androsta-3,5-diene-3-carboxylate [(I): Y═O, R₁═iPr, R₂═iPr, R₃═H, ═══double bond,

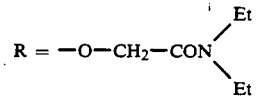

To a solution of 17β-[N-isopropyl-N-(N-isopropylcarbamoyl) carbamoyl]androsta-3,5-diene-3-carboxylic acid (480 mg) in anhydrous dimethylformamide (13 ml), maintained under nitrogen atmosphere and cooled to about 0° C. with an ice-bath, sodium hydride (41.1 mg of a 80% suspension in mineral oil) is added and the mixture is stirred at about 0° C. for 1 hour.

N,N-Diethyl-2-chloroacetamide (409.8 mg) and sodium iodide (410.6 mg) are added at 0° C. and then the mixture is stirred at room temperature for 3 hours.

As some starting material is still unreacted, a further amount of N,N-diethyl-2-chloroacetamide (132.9 mg) and sodium iodide (136.8 mg) are added and the mixture is stirred for additional 3 hours at room temperature.

The reaction mixture is poured into ice-water (250 ml) and extracted with toluene (4×50 ml); the combined organic extracts are treated with triethylamine (1 ml) and washed with water (3×20 ml), 0.1N sodium thiosulphate, brine and anhydrified over sodium sulphate.

After removing the solvent under vacuum, the crude dark oil so obtained (500 mg) is purified by flash chromatography on silica gel (eluant: n-hexane/ethyl acetate 40:60), so obtaining 380 mg of a slightly yellow solid material that is triturated with ether, so affording 320 mg of the title compound as a white solid material (m.p. 103°–105° C.).

Elemental analysis: calculated for $C_{34}H_{53}N_2O_5$ C 69.95 H 9.15 N 7.20 found C 69.42 H 9.41 N 7.03

NMR (CDCl₃) δ: 7.17 (m, 1H, H(4)), 6.51 (d, 1H, CONH), 5.85 (m, 1H, H(6)), 4.80 (s, 1H, COOCH₂CO), 4.48 (m, 1H,

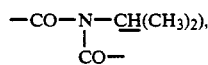

3.98 (m, 1H, CONHCH(CH(CH₃)₂), 3.38 [q, 4H, 2 CH₂CH₃), 1.35–1.15 (4d, 12H, 4 isopropylic CH₃), 0.90 (s, 3H, CH₃(19)), 0.80 (s, 3H, CH₃(18)).

MS (m/z): 498 M — O═C═N—CH(CH₃)₂⁻¹ +⁻ 367 M — O═C═N—CH(CH₃)₂ — Et₂NCO—CH₂OH⁻¹ +⁻ (100%)

EXAMPLE 10

1-(3-oxoandrost-4-one-17β-carbonyl)-3-tertbutylurea [compound (VI): Y═O, R₁═H, R₂═tBu, R₃═H]

To a mixture of 3-oxo-androst-4-ene-17β-carboxylic acid (284 mg) in anhydrous toluene (6.0 ml), oxalyl chloride (0.72 ml) is added dropwise.

The mixture is stirred at room temperature for 1.5 hours and then the volatiles are removed under vacuum, so obtaining a yellowish solid residue of 3-oxoandrost-4-ene-17β-carbonyl chloride.

To a solution of the acyl chloride so obtained in pyridine (4.1 ml), solid tertbutylurea (105 mg) is added.

After stirring for 2 hours, the reaction mixture is poured into ice-water (60 ml) and extracted with methylene chloride; the combined organic extracts are washed with 1N hydrochloric acid, brine, water and anhydrified over sodium sulphate.

Evaporation of the solvent leaves 330 mg of a dark solid which is chromatographed on silica gel (eluant: n-hexane/ethyl acetate 50:50), so affording 230 mg of the title compound (m.p. 210°–217° C.).

NMR (CDCl₃) δ: 8.5 (s, 1H, —CONH—), 8.1 (s, 1H, —CONH—), 5.7 (m, 1H, H(4)), 1.35 (s, 9H, tBu), 1.1 (s, 3H, CH₃(19)), 0.8 (s, 3H, CH₃(18).

Following an analogous procedure and using the appropriate starting materials, the compounds listed below can be prepared: (3-oxoandrost-4-ene-17β-carbonyl)urea (m.p. 242°–245° C.) and 1-(3-oxoandrost-4-ene-17β-carbonyl)-3-n-butylurea.

EXAMPLE 11

1-(3-oxoandrost-4-ene-17β-carbonyl)-3,3-diethylurea [compound (VI): Y═O, R₁═H, R₂═R₃═Et]

To a suspension of potassium hydride (275 mg) in anhydrous tetrahydrofurane (2 ml), under nitrogen atmosphere, solid N,N-diethylurea (110 mg) is added; the mixture is stirred at room temperature for 10 minutes, then it is refluxed for 2 hours.

After cooling at room temperature, the acyl chloride (prepared from 95.0 mg of 3-oxoandrost-4-ene-17β-carboxylic acid, following the procedure described in the example 10), dissolved in anhydrous tetrahydrofurane (2 ml) is added dropwise. The mixture is stirred at room temperature for 2 hours, the volatiles are removed under reduced pressure and the residue is taken up with ethyl acetate and water.

After acidification with 1N HCl, the organic layer is separated and the aqueous is extracted twice with ethyl acetate. The combined organic extracts are washed with water, anhydrified over sodium sulphate and evaporated under vacuum.

The crude so obtained (180 mg) is purified by flash chromatography on silica gel (eluant: n-hexane/ethyl acetate 75:25), so affording 80 mg of the title compound (m.p. 187°–190° C.).

NMR (CDCl₃) : 7.1 (s, 1H, —CONHCO—), 5.7 (m, 1H, H(4)), 3.3

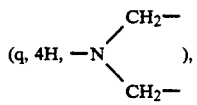

1.15 (t, 6H, 2 N—CH₂CH₃), 1.1 (s, 3H, CH₃(19)), 0.8 (s, 3H, CH₃(18)).

Following an analogous procedure and using the appropriate starting materials, 1-(3-oxoandrost-4-ene-17β-carbonyl)-3,3-dimethylurea, is prepared.

EXAMPLE 12

1-Methyl-1-(3-oxoandrost-4-ene-17β-carbonyl)-3,3-diethylurea compound (VI): Y═O, R₁═CH₃, R₂═R₃═Et]

To a suspension of potassium hydride (275 mg) in anhydrous tetrahydrofurane (2 ml), under nitrogen atmosphere, solid N,N-diethylurea (39 mg) is added; the mixture is stirred at room temperature for 10 minutes and then it is refluxed for 2 hours.

After cooling at room temperature, the acyl chloride (prepared from 95.0 mg of 3-oxoandrost-4-ene-17β-carboxylic acid, following the procedure described in the example 10), dissolved in anhydrous tetrahydrofurane (9 ml) is added dropwise over 5 minutes.

The mixture is stirred at room temperature for 1.5 hours and then methyl iodide (0.168 ml) is added dropwise. After stirring at room temperature for 1.5 h the reaction is cooled to about 0° C. and water is added slowly.

Extraction with ethyl acetate, anhydrification over sodium sulphate and evaporation of the solvent under vacuum affords 115 mg of a crude yellow oil that is purified by flash chromatography on silica gel (eluant: n-hexane/ethyl acetate 65:35), so obtaining 52 mg of the title compound (m.p. 142°–145° C.).

NMR (CDCl$_3$): 5.7 (m, 1H, H(4)), 3.3

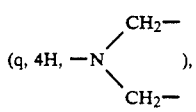

(q, 4H, —N⟨CH$_2$— / CH$_2$—⟩), 2.98 (s, 3H, N—CH$_3$), 1.15 (t, 6H, 2 N—CH$_2$CH$_3$), 1.1 (s, 3H, CH$_3$(19)), 0.8 (s, 3H, CH$_3$(18)).

Following an analogous procedure and using the appropriate starting materials, the compounds listed below are prepared:
1-Ethyl-1-(3-oxoandrost-4-ene-17β-carbonyl)-3,3-diethylurea;
1-Methyl-1-(3-oxoandrost-4-ene-17β-carbonyl)-3,3-dimethylurea and
1-Ethyl-1-(3-oxoandrost-4-ene-17β-carbonyl)-3,3-dimethylurea.

FORMULATION EXAMPLE

Scored tablets for oral use, each containing 250 mg of the active substance, were manufactured as follows.

| Composition (for 10,000 tablets) | |
|---|---|
| 17β-[N-isopropyl-N-(N-isopropylcarbamoyl)carbamoyl]androst-3,5-diene-3-carboxylic acid; | 2500 g |
| corn starch | 275 g |
| talc powder | 187 g |
| calcium stearate | 38 g |

The active substance was granulated with a 4% w/v aqueous solution of methyl cellulose.

To the dried granules a mixture of the remainder of the ingredients is added and the final mixture compressed into tablets of proper weight.

What is claimed is:

1. A compound of the following formula (I)

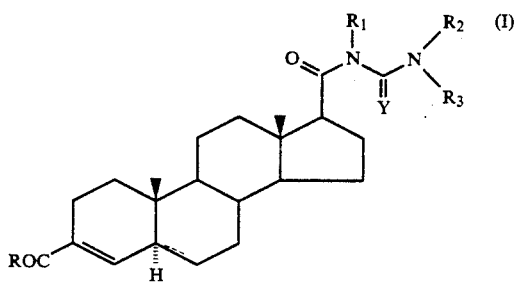

wherein
Y is oxygen or sulphur;
R is a group:
  a) —OR$_4$, wherein R$_4$ is hydrogen or a C$_1$–C$_6$ alkyl group;
  b)

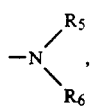

wherein each of R$_5$ and R$_6$, independently, is hydrogen or a C$_1$–C$_6$ alkyl group;
  c)

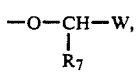

wherein R$_7$ is hydrogen or a C$_1$–C$_6$ alkyl group and W is a group:
  (i)

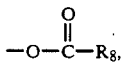

wherein R$_8$ is a C$_1$–C$_6$ alkyl group, a C$_5$–C$_6$ cycloalkyl group, a C$_6$–C$_9$ cycloalkylalkyl group, a phenyl group or a benzyl group; or
  (ii)

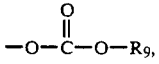

wherein R$_9$ is a C$_1$–C$_6$ alkyl group or a C$_5$–C$_6$ cycloalkyl group; or
  (iii)

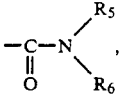

wherein R$_5$ and R$_6$ are as defined above;
  d)

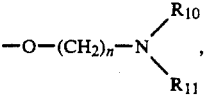

wherein each of R$_{10}$ and R$_{11}$ is, independently, hydrogen or a C$_1$–C$_6$ alkyl group or taken together with the nitrogen atom to which they are linked form a pentatomic or hexatomic saturated heteromonocyclic ring, selected from oxygen and nitrogen and n is an integer from 2 to 4;
R$_1$ is hydrogen, a C$_1$–C$_6$ alkyl group, a C$_5$–C$_6$ cycloalkyl group, a C$_6$–C$_9$ cycloalkyalkyl group or an aryl group;
each of R$_2$ and R$_3$ is, independently, selected from the group consisting of hydrogen, C$_1$–C$_6$ alkyl, C$_5$–C$_6$ cycloalkyl, C$_6$–C$_9$ cycloalkylalkyl and aryl or R$_2$ and R$_3$, taken together with the nitrogen atom to which they are linked, form a pentatomic or hexatomic saturated heteromonocyclic ring, optionally containing at least one additional heteroatom selected from oxygen and nitrogen; and the symbol ═ represents a single or a double bond provided that when it is a double bond the hydrogen in the 5α position does not exist and the pharmaceutically acceptable salts thereof.

2. A compound of formula I, according to claim 1 wherein Y is oxygen or sulphur;
R is OH, OCH$_3$, O CH$_2$CH$_3$, $$-N(CH_3)_2, \quad -N(C_2H_5)_2, \quad -O-CH_2-O-\overset{O}{\underset{\|}{C}}-CH_3,$$

$$-O-CH_2-O-\overset{O}{\underset{\|}{C}}-\overset{CH_3}{\underset{CH_3}{\overset{|}{C}}}-CH_3,$$

$$-O-CH_2-O-\overset{O}{\underset{\|}{C}}-O-C_2H_5,$$

$$-O-CH_2-\overset{O}{\underset{\|}{C}}-N(C_2H_5)_2,$$

$$-O-CH_2-CH_2-N\begin{pmatrix}\\ \\ \end{pmatrix}O;$$

R$_1$ is methyl, ethyl, isopropyl, tert-butyl, cyclohexyl; the group $$-N\diagdown\begin{matrix}R_2\\R_3\end{matrix} \text{ is:}$$

$$-N\diagdown\begin{matrix}H\\\text{cyclohexyl}\end{matrix}; -N\diagdown\begin{matrix}H\\CH_3\end{matrix}; -N\diagdown\begin{matrix}H\\C_2H_5\end{matrix}; -N\diagdown\begin{matrix}H\\CH(CH_3)_2\end{matrix};$$

$$-N\diagdown\begin{matrix}H\\C(CH_3)_3\end{matrix}; -N\diagdown\begin{matrix}CH_3\\CH_3\end{matrix}; \text{ or } -N\diagdown\begin{matrix}C_2H_5\\C_2H_5\end{matrix};$$

the symbol ═ represents a single or double bond, and the pharmaceutically acceptable salts thereof.

3. A compound selected from the group consisting of:
17β-[N-isopropyl-N-(N-isopropylcarbamoyl)carbamoyl]androsta-3,5-diene-3-carboxylic acid;
17β-[N-cyclohexyl-N-(N-cyclohexylcarbamoyl)carbamoyl]androsta-3,5-diene-3-carboxylic acid;
17β-[N-tert-butyl-N-(N-tert-butylcarbamoyl)carbamoyl]androsta-3,5-diene-3-carboxylic acid;
17β-[N-isopropyl-N-(N-isopropylthiocarbamoyl)carbamoyl]androsta-3,5-diene-3-carboxylic acid;
17β-[N-cyclohexyl-N-(N-cyclohexylthiocarbamoyl)carbamoyl]androsta-3,5-diene-3-carboxylic acid;
17β-[N-methyl-N-(N,N-diethylcarbamoyl)carbamoyl]androsta-3,5-diene-3-carboxylic acid;
methyl 17β-[N-isopropyl-N-(N-isopropylcarbamoyl)carbamoyl]androsta-3,5-diene-3-carboxylate;
methyl 17β-[N-isopropyl-N-(N-isopropylthiocarbamoyl)carbamoyl]androsta-3,5-diene-3-carboxylate;
methyl 17β-[N-cyclohexyl-N-(N-cyclohexylcarbamoyl)carbamoyl]androsta-3,5-diene-3-carboxylate;
methyl 17β-[N-cyclohexyl-N-(N-cyclohexylthiocarbamoyl)carbamoyl]androsta-3,5-diene-3-carboxylate;
methyl 17β-[N-tert-butyl-N-(N-tert-butylcarbamoyl)carbamoyl]androsta-3,5-diene-3-carboxylate;
methyl 17β-[N-methyl-N-(N,N-diethylcarbamoyl)carbamoyl]androsta-3,5-diene-3-carboxylate;
N,N-diethyl 17β-[N-isopropyl-N-(N-isopropylcarbamoyl)carbamoyl]androsta-3,5-diene-3-carboxamide;
N,N-diethyl 17β-[N-isopropyl-N-(N-isopropylthiocarbamoyl)carbamoyl]androsta-3,5-diene-3-carboxamide;
N,N-diethyl 17β-[N-cyclohexyl-N-(N-cyclohexylcarbamoyl)carbamoyl]androsta-3,5-diene-3-carboxamide;
N,N-diethyl 17β-[N-cyclohexyl-N-(N-cyclohexylthiocarbamoyl)carbamoyl]androsta-3,5-diene-3-carboxamide;
N,N-diethyl 17β-]N-methyl-N-(N,N-diethylcarbamoyl)carbamoyl]androsta-3,5-diene-3-carboxamide;
Acetyloxymethyl 17β-[N-isopropyl-N-(Nisopropylcarbamoyl)carbamoyl]androsta-3,5-diene-3-carboxylate;
Pivaloyloxymethyl 17β-[N-isopropyl-N-(N-isopropylcarbamoyl)carbamoyl]androsta-3,5-diene-3-carboxylate;
Ethoxycarbonyloxymethyl 17β-[N-isopropyl-N-(N-isopropylcarbamoyl)carbamoyl]androsta-3,5-diene-3-carboxylate;
(N,N-diethylcarbamoyl)methyl 17β-[N-isopropyl-N-(N-isopropylcarbamoyl)carbamoyl]androsta-3,5-diene-3-carboxylate;
2-(N-morpholino)ethyl 17β-[N-isopropyl-N-(N-isopropylcarbamoyl)carbamoyl]androsta-3,5-diene-3-carboxylate;
and, the pharmaceutically acceptable salts thereof.

4. A pharmaceutically composition comprising a pharmaceutically acceptable carrier and/or diluent and, as an active principle, an effective amount of a compound of formula (I) according to claim 1 or a pharmaceutically acceptable salt thereof.

5. A method of producing testosterone 5α-reductase inhibition in a patient in need thereof, said method comprising administering to the said patient an effective amount of a composition according to claim 4.

6. A method of producing testosterone 5α-reductase inhibition in a patient in need thereof, said method comprising administering to the said patient an effective amount of a compound of formula (I) according to claim 1.

* * * * *

UNITED STATES PATENT AND TRADEMARK OFFICE
CERTIFICATE OF CORRECTION

PATENT NO. : 5,212,166
DATED : May 18, 1993
INVENTOR(S) : Achille PANZERI et al

It is certified that error appears in the above-identified patent and that said Letters Patent is hereby corrected as shown below:

On the title page, Item [54], Line 1, and col. 1, line 1, change "SUBSITUTED" to-- SUBSTITUTED-- .

Title page, item [57],
    In the Abstract, Formula (I), change:                                         to:

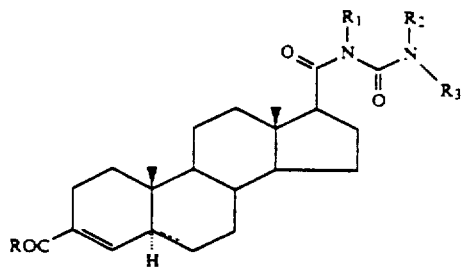     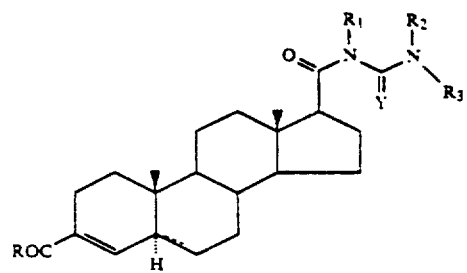

Column 1, Line 62, change "5=-reduc-" to -- 5α-reduc- --.

UNITED STATES PATENT AND TRADEMARK OFFICE
CERTIFICATE OF CORRECTION

PATENT NO. : 5,212,166

DATED : May 18, 1993

INVENTOR(S) : Achille PANZERI et al

It is certified that error appears in the above-identified patent and that said Letters Patent is hereby corrected as shown below:

Column 15, Example 2, in the Formula, Lines 40 to 44, change:                         to:

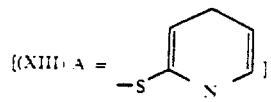  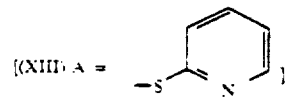

Column 24, Claim 1, Line 59, before "selected from", insert -- optionally containing at least one additional heteroatom --.

UNITED STATES PATENT AND TRADEMARK OFFICE
CERTIFICATE OF CORRECTION

PATENT NO. : 5,212,166
DATED : May 18, 1993
INVENTOR(S) : Achille Panzeri, et. al.

It is certified that error appears in the above-indentified patent and that said Letters Patent is hereby corrected as shown below:

Column 24, claim 1, line 59, before "selected from",
insert --Optionally containing at least one additional heteroatom--.

Signed and Sealed this

Fifteenth Day of March, 1994

Attest:

BRUCE LEHMAN

Attesting Officer

Commissioner of Patents and Trademarks